United States Patent [19]

Hayes et al.

[11] Patent Number: 4,562,065

[45] Date of Patent: Dec. 31, 1985

[54] ASTRINGENT DENTIFRICE

[75] Inventors: Harry Hayes, Thelwall; Kenneth Harvey, Wilmslow, both of England

[73] Assignee: Colgate-Palmolive Company, New York, N.Y.

[21] Appl. No.: 680,425

[22] Filed: Dec. 11, 1984

[51] Int. Cl.[4] ............................................. A61K 9/16
[52] U.S. Cl. ................................................... 424/49
[58] Field of Search .................................. 424/49-58

[56] References Cited

U.S. PATENT DOCUMENTS

| | | | |
|---|---|---|---|
| 3,538,230 | 11/1970 | Pader et al. | 424/50 |
| 3,828,977 | 8/1974 | Borchert | 222/95 |
| 3,838,796 | 10/1974 | Cohen | 222/105 |
| 3,932,606 | 1/1976 | Barth et al. | 424/52 |
| 3,939,261 | 2/1976 | Barth | 424/49 |
| 4,022,880 | 5/1977 | Vinson et al. | 424/49 |
| 4,082,841 | 4/1978 | Pader | 424/50 |
| 4,100,269 | 7/1978 | Pader | 424/49 |
| 4,138,477 | 2/1979 | Gaffar | 424/52 |
| 4,144,323 | 3/1979 | Lamberti | 424/54 |
| 4,153,680 | 5/1979 | Seybert | 424/49 |
| 4,160,821 | 7/1979 | Sipos | 424/49 |
| 4,171,757 | 10/1979 | Diamond | 222/389 |
| 4,339,432 | 7/1982 | Ritchey et al. | 424/54 |
| 4,396,599 | 8/1983 | Sipos | 424/52 |
| 4,416,867 | 11/1983 | Ritchey et al. | 424/49 |
| 4,425,325 | 1/1984 | Ritchey et al. | 424/54 |
| 4,435,380 | 3/1984 | Pader | 424/49 |
| 4,456,585 | 6/1984 | Hayes et al. | 424/49 |
| 4,469,674 | 9/1984 | Shah et al. | 424/52 |

FOREIGN PATENT DOCUMENTS

| | | |
|---|---|---|
| 2038303 | 7/1980 | United Kingdom . |
| 1572864 | 8/1980 | United Kingdom . |
| 2070695 | 9/1981 | United Kingdom . |

*Primary Examiner*—Shep K. Rose
*Attorney, Agent, or Firm*—Robert L. Stone; Herbert S. Sylvester; Murray M. Grill

[57] ABSTRACT

Astringent dentifrice containing a water-soluble zinc salt and a hydrous silica gel polishing agent compatible and substantially non-reactive with the zinc salt.

10 Claims, No Drawings

ASTRINGENT DENTIFRICE

This invention relates to a dentifrice containing a water-soluble zinc salt which provides an astringent effect on oral mucosa and periodontal tissue during toothbrushing.

The astringent effectiveness of zinc ions provided by water-soluble zinc salts to promote and improve oral hygiene has long been known. Nevertheless, there have been limits on the practical use of zinc in dentifrice compositions since zinc ions can readily react with typical dentifrice components causing substantial loss of availability of zinc ions.

For instance, siliceous polishing agent is often employed in dentifrice gel compositions prepared for toothbrushing. Such siliceous polishing agents as silica xerogel having an average particle size between about 2 and 20 microns and generally a surface area of at least about 300 m$^2$/gm, typically about 300–370 m$^2$/gm, or about 600–800 m$^2$/gm, which are described in U.S. Pat. No. 3,538,230 to Pader et al, undergo in situ reaction with zinc ion so that much of the theoretically available zinc is lost by physio-chemical means such as absorption. Similar compatibility problems would occur when water-soluble zinc salt is present together with other dentifrice salt polishing agents, particularly calcium salts such as dicalcium phosphate or calcium carbonate. In fact, it has been believed that it would be difficult to employ water-soluble zinc salt and maintain high level of availability of zinc ions in such conventional dentifrices.

It has therefore been difficult to prepare dentifrices containing amounts of zinc ions which remain effective in providing astringent properties. In particular, gel-type dentifrices providing zinc astringency have not been available due to the incompatibility of zinc ion with various siliceous polishing agents.

In the present invention, use is made of a precipitated, amorphous silica gel which has been described in British Published Patent Application No. 2 038 303 A to Feig et al and in co-pending commonly assigned U.S. patent application Ser. No. 576,046, filed Feb. 1, 1984. Such material is available from Grace G.m.b.H. as product such as Syloblanc 81, Syloblanc 81C and Syloblanc 82. It is distinct from the types of xerogel which have been sold by W. R. Grace and Co. under the trademark Syloid and which are particularly described in U.S. Pat. No. 3,538,230 to Pader et al. Indeed, although some products sold by Grace G.m.b.H. under the trademark Syloblanc were formerly or are still available under the trademark Syloid, none of Syloblanc 81, Syloblanc 81C or Syloblanc 82 have ever been available under the trademark Syloid. It is particularly noteworthy that the grades of the silica gel employed in the present invention are less abrasive as the surface area increases whereas the grades of silica xerogel which are described in U.S. Pat. No. 3,538,230 are generally more abrasive as their surface area increases.

In view of the low compatibility of most polishing agents with zinc including those polishing agents of U.S. Pat. No. 3,538,230, it was quite unexpected that a particular siliceous polishing material would not have such a problem. Nevertheless, in accordance with the present invention, it has been found that retention of high levels of astringency from zinc ions is attained when such particular siliceous polishing material is employed.

It is an advantage of this invention that an astringent dentifrice containing zinc ions is provided.

It is a further advantage of this invention that an astringent gel-type toothpaste containing zinc ions is provided.

Further advantages of the invention will be apparent from consideration of the following specification.

In accordance with certain of its aspects, this invention relates to an astringent dentifrice comprising about 20–90% by weight of liquid vehicle comprising water in amount of at least about 3% by weight of said dentifrice, about 0.05–5% by weight of a gelling agent and about 10–50% by weight of a polishing agent comprising a synthetic precipitated, amorphous silica gel having an average particle size of 1 to 30 microns and
(a) surface area of 1 to 600 m$^2$/g,
(b) a pore volume of 0.05 to 0.5 cm$^3$/g,
(c) a product of surface area (in m$^2$/g) × pore volume (in cm$^3$/g) less than or equal to 240,
(d) a calculated pore diameter of 1.5 to 2.5 nm and
(e) a water content of less than 25% by weight; and
up to about 5% of a water-soluble zinc salt which provides at least about 50 ppm of zinc ions to said dentifrice.

As indicated above, the synthetic precipitated silica is of the type described in British Published Patent Application No. 2 038 303 A and U.S. patent application Ser. No. 576,046. Specific grades of the silica material described therein are suitable for use in the practice of the present invention. Further, specific grades which are particularly preferred are described in an October, 1980, trade publication of Grace G.m.b.H. of Norderstadt, Germany, as Syloblanc 81 and Syloblanc 82 as having the following typical physical and chemical characteristics:

|  | SYLOBLANC 81 | SYLOBLANC 82 |
| --- | --- | --- |
| Average particle size (according to Coulter) μm | 4 | 7 |
| Wet screen residue (42 μm) % | 0.02 | 0.02 |
| pH (5% suspension in water) | 3 | 6 |
| Surface area (B.E.T.) m$^2$/g | 400 | 480 |
| Loss on drying % | 7 | 4 |
| SiO$_2$ content (on ignited substance) % | 96 | 99 |
| Refractive index | 1.46 | 1.46 |

In a variation of Syloblanc 81 available as Syloblanc 81C, the pH (5% suspension in water) is about 6–8.

Syloblanc 81 and 81C, in particular are highly effective in polishing dental surfaces. Syloblanc 82 is lower in polishing effect but can be used by consumers desiring such reduced effect. Likewise, grades of the silica material may be proportioned in mixtures to produce appropriate polishing characteristics. It is noteworthy that the dentifrices are compatible in unlined aluminium dentifrice tubes even in the absence of phytate salt, which is necessary in the invention described in U.S. patent application Ser. No. 576,046. The precipitated amorphous silica gel is employed in amount of about 10–50% by weight, typically about 10–40% in a gel dentifrice.

Aqueous slurries of the silica materials (e.g. about 5 to 20% slurries) typically have a pH of about 2 to 9. Since the dentifrice composition of the present invention preferably has a pH (measured in 20% aqueous slurry) of at least about 5.5, e.g. about 5.5–7.5, the pH of the dentifrice may be adjusted with an appropriate material such as sodium hydroxide, etc.

The water-soluble zinc salt is present in the dentifrice in amount of up to about 5% by weight, preferably about 0.01–3% and most preferably about 0.1–2%. Water-soluble zinc salts in accordance with the present invention are at least about 10% by weight, preferably at least about 20%, soluble in water. There is provided at least about 50 ppm of zinc ions to the dentifrice, preferably at least about 750 ppm and most preferably at least about 1000 ppm of zinc ions. Suitable zinc salts include zinc sulphate, zinc chloride, zinc bromide, zinc iodide, zinc nitrate and zinc acetate. In the case of zinc chloride, 0.01% by weight provides about 50 ppm of zinc ions and 0.2% by weight provides about 1000 ppm of zinc ions. 0.48% by weight of zinc sulphate, heptahydrate provides about 1000 ppm of zinc ions. In addition, zinc oxide, a sparingly soluble (below 0.0005%) zinc compound may also be added to prevent a lowering of the pH in the product. This acts as a buffer system and improves pH stability and compatibility in unlined aluminium tubes. It may be present in amount of about 0.005–0.5% by weight.

The dentifrice comprises a liquid vehicle containing about 3–60% by weight of water, typically mixed with at least one humectant. The liquid phase comprises about 20–90% by weight of the dentifrice and is generally about 25–80% liquid, typically with about 3–50% by weight, preferably about 3–10%, of water in a substantially clear gel dentifrice or gel dentifrice which would be substantially clear except for the presence of an opacifying agent, such as titanium dioxide, and about 11–50% of water in a hazy to opaque gel dentifrice, with about 10–90% by weight, preferably about 15–80%, of humectant. Typical humectants include glycerine, sorbitol (e.g. 70% solution), maltitol, polyethylene glycol of molecular weight of about 400–600, propylene glycol and mixtures thereof.

The dentifrice also contains a gelling or binding agent as a solid vehicle agent, although this may be in small amount, since the synthetic, precipitated silica can effect a thickening or gelling of the dentifrice into a creamy or pasty consistency. Gelling or binding agents include xanthan, Irish moss, iota-carrageenan, gum tragacanth, hydroxyethyl cellulose, hydroxypropyl cellulose, polyvinyl pyrrolidone, starch and mixtures thereof. Gelling agents may be used in amount of about 0.05–5% by weight, typically about 0.05–2% and preferably about 0.1–1.5%.

Any suitable surface active or detersive material may be included in the dentifrice compositions. Such compatible materials are desirable to provide additional detersive foaming and antibacterial properties depending upon the specific type of surface active material and are selected similarly. These detergents are water-soluble compound usually, and may be anionic, nonionic, amphoteric or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dedecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

Other particularly suitable surface-active materials include nonionic agents such as condensates of sorbitan monostearate with approximately 20 moles of ethylene oxide, condensates of ethylene oxide with propylene oxide, condensates of propylene glycol ("Pluronic" materials) and amphoteric agents such as long chain (alkyl)amide-alkylene-alkalated amine derivatives, which are available under the trademark "Miranol" C$_2$M. Cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12–18 carbon atoms) and two (poly)oxyethylene groups attached to the nitrogen (typically containing a total of from about 2 to 50 ethanoxy groups per molecule) and salts thereof with acids, and compounds of the structure

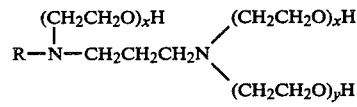

wherein R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the oral preparation of the present invention.

Various other materials may be incorporated in the dental creams of this invention. Examples thereof are opacifiers, preservatives, stabilizers, silicones, chlorophyll compounds and ammoniated materials such as urea, diammonium phosphate and mixtures thereof. These adjuvants are incorporated in the instant compositions in amounts which do not substantially adversely affect the desired properties and characteristics and are suitably selected and used in conventional amounts.

For some purposes it may be desirable to include antibacterial agents in the compositions of the present invention. Typical antibacterial agents which may be used in amount of about 0.01% to about 5%, preferably about 0.05 to about 1.0%, by weight of the dentifrice composition include cetyl pyridinium chloride, benzethonium chloride as well as:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium)5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate, sodium saccharine, dipeptides of U.S. Pat. No. 3,939,261 and oxathiazin salts of U.S. Pat. No. 3,932,606. Suitable flavor and sweetening agents may together comprise from about 0.01 to 5% or more of the composition.

The dentifrice is packaged in a container from which it can be readily extruded such as a pressure differential or mechanically operated dental cream dispenser or a lined or unlined aluminium tube or wax lined lead tube or plastic tube, which may be laminated with aluminum. The rheological properties are highly desirable when a mechanically operated dispensing container of the type described in British Patent Application No. 2,070,695A, published Sept. 9, 1981, is employed. This dispensing container comprises a dispensing mouthpiece, a tension member, a central rod, a piston and operating hand control. The disclosure of this published application is incorporated herein by reference.

Pressure differential dispensing container may be of the aerosol or vacuum type. Suitable pressure differential dispensers include those comprising a collapsible product-containing bag being disposed within a rigid container which contains a propellant fluid. In such dispensing containers, operation of the valve permits release of the product only, the propellant fluid being separated from the product by the fluid impermeable bag. Dispensers of this type are described in U.S. Pat. Nos. 3,828,977 and 3,838,796. These are the so-called Sepro dispensers. So-called Exxel and Enviro Spray containers also utilize pressure.

Still another type dispenser is the barrier piston container described in U.S. Pat. No. 4,171,757. Such container includes a valve, a product-containing compartments and an essentially fluid-tight barrier piston which separates the propellant fluid from the contained product (the so-called Diamond container).

The dentifrice is typically prepared by forming a premix of the gelling agent with the liquid vehicle components, e.g. water and humectant, which may also contain additional ingredients such as sweetener, and blending therewith the synthetic precipitated silica gel and zinc salt. If employed, additional ingredients may then be added.

Although the invention is described with regard to illustrative examples, it will be apparent to one skilled in the art that various modifications may be made thereto which fall within its scope. All amounts are by weight unless otherwise indicated.

EXAMPLE 1

The following opacified gel dentifrices are prepared and placed in unlined aluminium tubes:

|  | PARTS | |
| --- | --- | --- |
|  | A | B |
| Glycerine | 25.000 | 25.000 |
| Sorbitol (70%) | 47.050 | 43.830 |
| Xanthan | 0.260 | 0.260 |
| Sodium saccharin | 0.170 | 0.170 |
| Titanium dioxide | 1.000 | 1.000 |
| Water | 3.000 | 3.000 |
| Zinc sulphate heptahydrate | 0.480 | 0.480 |
| Precipitated amorphous silica gel* | 20.000 | — |
| Silica xerogel** | — | 17.000 |
| Silica aerogel*** | — | 6.500 |
| Sodium hydroxide (40%) | 0.280 | — |
| Sodium lauryl sulphate | 1.760 | 1.760 |
| Flavour | 1.000 | 1.000 |
| pH (20% slurry) | 5.9 | 6.1 |

*Syloblanc 81 available from Grace G.m.b.H.;
**Syloid AL1 available from Grace G.m.b.H., formerly known as Syloid 63.

The theoretical amount of soluble zinc ions in each gel dentifrice is 1000 ppm or 0.100%.

Dentifrice A does not require the presence of thickener material to provide desirable gel character. Its consistency is about equivalent to that of dentifrice B.

Each dentifrice is aged at room temperature and at 43° C. Both retain generally equivalent desirable consistencies. The percentage amounts of available soluble zinc ions in each dentifrice is determined to be as follows:

|  | % $Zn^{+2}$-Room Temperature | | | 43° C. | | |
| --- | --- | --- | --- | --- | --- | --- |
|  | Initial | 1 month | 3 months | two weeks | one month | three months |
| Dentifrice A | 0.084 | 0.080 | 0.050 | 0.091 | 0.070 | 0.050 |
| Dentifrice B | 0.054 | 0.042 | 0.005 | 0.049 | 0.048 | 0.005 |

Dentifrice A containing Syloblanc 81 retains superior levels of soluble zinc ions compared to the otherwise generally equivalent Dentifrice B containing Syloblanc AL1.

Similar superior levels of retention of soluble zinc ions are attained when Syloblanc 81 of the dentifrice A is replaced with Syloblanc 82 and with a 1:1 mixture of Syloblanc 81 and 82, in each, with levels of sodium hydroxide reduced or omitted, with their amounts added to sorbitol (70%).

Likewise, superior retention levels of soluble zinc ions are attained when Syloblanc 81 is replaced with Syloblanc 81C, with sodium hydroxide omitted and its amount added to sorbitol (70%).

0.25 parts of zinc oxide are incorporated into each of dentifrices A and B, in place of corresponding amounts of sorbitol, thereby stabilising the pH during aging and improving compatibility with unlined aluminium tubes for prolonged periods.

EXAMPLE 2

The following stable visually clear gel dentifrices are prepared and placed in unlined aluminium tubes:

| | PARTS | | | |
|---|---|---|---|---|
| | A | B | C | D |
| Glycerin | 25.000 | 25.000 | 25.000 | 25.000 |
| Sorbitol (70%) | 48.310 | 48.590 | 48.590 | 48.450 |
| Xanthan | 0.260 | 0.260 | 0.260 | 0.260 |
| Sodium saccharin | 0.170 | 0.170 | 0.170 | 0.170 |
| Water | 3.000 | 3.000 | 3.000 | 3.000 |
| Zinc chloride | 0.020 | 0.020 | 0.020 | 0.020 |
| Syloblanc 81 | 20.000 | — | — | 10.000 |
| Syloblanc 81C | — | 20.000 | — | — |
| Syloblanc 82 | — | — | 20.000 | 10.000 |
| Sodium hydroxide (40%) | 0.280 | — | — | 0.140 |
| Sodium lauryl sulphate | 1.760 | 1.760 | 1.760 | 1.760 |
| Flavour | 1.000 | 1.000 | 1.000 | 1.000 |
| Blue colour solution (1%) | 0.200 | 0.200 | 0.200 | 0.200 |

EXAMPLE 3

The following hazy and opaque gel dentifrices are prepared and packaged in mechanically operated dispensing containers:

| | PARTS | | | |
|---|---|---|---|---|
| | A | B | C | D |
| Glycerine | 25.000 | 25.000 | 25.000 | 25.000 |
| Sorbitol (70%) | 24.970 | 24.870 | 24.870 | 24.870 |
| Iota carrageenan | 0.700 | 0.700 | 0.700 | 0.700 |
| Sodium saccharin | 0.170 | 0.170 | 0.170 | 0.170 |
| Water | 25.000 | 25.000 | 25.000 | 25.000 |
| Zinc bromide dihydrate | 0.400 | — | — | — |
| Zinc iodide | — | 0.500 | — | — |
| Zinc nitrate hexahydrate | — | — | 0.500 | — |
| Zinc acetate dihydrate | — | — | — | 0.500 |
| Syloblanc 81C | 21.000 | 21.000 | 21.000 | 21.000 |
| Sodium lauryl sulphate | 1.760 | 1.760 | 1.760 | 1.760 |
| Flavour | 1.000 | 1.000 | 1.000 | 1.000 |

In the examples sodium cyclamate may replace sodium saccharin.

It will be apparent to those skilled in the art that further modifications of the examples illustrative of the invention may be made thereto.

We claim:

1. An astringent dentifrice comprising about 20–90% by weight of liquid vehicle comprising water in amount of at least about 3% by weight of said dentifrice, about 0.5–5% by weight of a gelling agent and about 10–50% by weight of a polishing agent comprising a synthetic precipitated, amorphous silica gel having an average particle size of 1 to 30 microns and
   (a) a surface area of 1 to 600 $m^2/g$,
   (b) a pore volume of 0.05 to 0.5 $cm^3/g$,
   (c) a product of surface area (in $m^2/g$) × pore volume (in $cm^3/g$) less than or equal to 240,
   (d) a calculated pore diameter of 1.5 to 2.5 nm and
   (e) a water content of less than 25% by weight; and
   up to about 5% of a water-soluble zinc salt which provides at least about 50 ppm of zinc ions to said dentifrice.

2. The astringent dentifrice claimed in claim 1 wherein said zinc salt is present in amount of 0.01–3% by weight.

3. The astringent dentifrice claimed in claim 1 wherein said zinc salt is selected from the group consisting of zinc sulphate, zinc chloride, zinc bromide, zinc iodide, zinc nitrate and zinc acetate.

4. The astringent dentifrice claimed in claim 3 wherein said zinc salt is zinc sulphate heptahydrate.

5. The astringent dentifrice claimed in claim 3 wherein said zinc salt is zinc chloride.

6. The astringent dentifrice claimed in claim 1 wherein said water in said liquid vehicle comprises about 3–10% by weight of said dentifrice and said synthetic amorphous silica gel comprises about 10–40% by weight of said dentifrice.

7. The astringent dentifrice claimed in claim 1 wherein said water in said liquid vehicle comprises about 11–50% by weight of said dentifrice.

8. The astringent dentifrice claimed in claim 1 wherein said synthetic amorphous silica gel is selected from the group having characteristics consisting of:

| | a | b | c |
|---|---|---|---|
| Average particle size (according to Coulter) μm | 4 | 7 | 4 |
| Wet screen residue (42 μm) % | 0.02 | 0.02 | 0.02 |
| pH (5% suspension in water) | 3 | 6 | 6–8 |
| Surface are (B.E.T) $m^2/g$ | 7 | 4 | 7 |
| Loss in drying % | 7 | 4 | 7 |
| $SiO_2$ content (on ignited substance) | 96 | 99 | 96 |
| Refractive index | 1.46 | 1.46 | 1.46 | and (d) mixtures thereof.

9. The astringent dentifrice claimed in claim 1 wherein said dentifrice is packaged in an unlined aluminium tube.

10. The astringent dentifrice claimed in claim 1 wherein said dentifrice also contains about 0.005–0.5% by weight of zinc oxide.

* * * * *